United States Patent

Kaufman

[11] 3,972,329
[45] Aug. 3, 1976

[54] BODY ELECTRODE FOR ELECTRO-MEDICAL USE

[76] Inventor: John G. Kaufman, 858 Condor Drive, Burlington, Ontario, Canada

[22] Filed: Nov. 25, 1974

[21] Appl. No.: 526,681

[52] U.S. Cl. ............................ 128/2.06 E; 128/417; 128/418; 128/DIG. 4
[51] Int. Cl.² .......................................... A61B 5/04
[58] Field of Search ....... 128/2.06 E, 2.1 E, DIG. 4, 128/404, 410, 411, 416–418

[56] References Cited
UNITED STATES PATENTS

| | | | |
|---|---|---|---|
| 1,212,541 | 1/1917 | Morse | 128/417 |
| 1,662,446 | 3/1928 | Wappler | 128/416 |
| 3,151,619 | 10/1964 | Sullivan | 128/DIG. 4 |
| 3,590,810 | 7/1971 | Kopecky | 128/2.06 E |
| 3,774,592 | 11/1973 | Lahr | 128/2.1 E |
| 3,817,252 | 6/1974 | Maurer | 128/417 |
| 3,828,766 | 8/1974 | Krasnow | 128/2.1 E |

FOREIGN PATENTS OR APPLICATIONS

| | | | |
|---|---|---|---|
| 675,494 | 12/1963 | Canada | 128/417 |
| 122,258 | 2/1972 | Denmark | 128/2.06 E |

OTHER PUBLICATIONS

"Fiber Stretches Graphite Use", Chemical Engineering, May 4, 1959, vol. 66, No. 9, p. 70.

*Primary Examiner*—Robert W. Michell
*Assistant Examiner*—Lee S. Cohen
*Attorney, Agent, or Firm*—Robert G. Hirons

[57] ABSTRACT

This disposable body electrode is constructed so that it can be stretched taut over a portion of a person's body to provide both secure attachment and uniformly good electrical contact thereto. The electrode includes an elastic cover sheet, a smaller flexible metallic sheet provided with a male snap fastener protruding through the cover sheet, and a stretchable, porous inner sheet all secured together at one end of the electrode. At the opposite end, only the cover sheet and inner sheet are secured together, thereby leaving the major area of the metallic sheet unsecured between them. An adhesive area is provided at each end of the inner surface of the inner sheet for removably attaching the electrode to the body.

10 Claims, 2 Drawing Figures

BODY ELECTRODE FOR ELECTRO-MEDICAL USE

BACKGROUND OF THE INVENTION

1. Field of Invention

The present invention relates to body electrodes, and more particularly to a disposable electrode for use with electro-medical equipment for surgery, therapy and diagnosis such as electrosurgical units, electrocardiographs, monitoring apparatus and ultrasound units.

2. Description of the Prior Act

The electrosurgical unit return electrode provides half of the circuit between the electrosurgical unit and patient. The current must be distributed over a sufficiently large area at the return electrodes to eliminate heating effects.

This reduction of current density (milliamperes) is provided by adequately sized electrodes and by good electrical contact between the return electrode and the patient. The return electrode should reduce the current density so that tissue burns do not occur at the electrode site.

Metal plate-type electrodes have traditionally been used as return body electrodes. Conventional reusable stainless steel return electrodes are not without problems due to design limitations and frequent handling, cleaning and reuse. Some problems are: return cable breakage, return electrode damage (distortion, bending, etc.), difficulty in placement on patient, tissue damage due to damaged plates, storage difficulty, and the unpleasant sensation caused by contact with a metallic plate.

Disposable return electrodes eliminate some of these problems. There are two types of disposable return body electrodes, namely, plate-type and adhesive-type. The present invention relates to an electrode of the latter type.

Because disposable return electrodes are used only once, the probability of physical damage is minimized. No cleaning, sterilization or restorage is required. Some problems of electrode placement (on the body), such as tissue necrosis and excessive heating are eliminated.

Adhesive-backed return electrodes should be capable of remaining securely attached for at least eight hours. Moreover, they typically require minimum skin preparation, and facilitate intentional removal following the operation.

The adhesive should be strong enough to prevent electrode movement while resisting stresses from the electrical return cable applied at its connection to the electrode.

The occurrence of a relatively small contact area between the patient and the conducting element, which can arise when the electrode does not tightly and intimately conform to the adjacent portion of the body, may cause the flow of current to produce undesirable heating or burning. Electrical conducting wetting agents such as electrosurgical gels have been developed to improve the electrical coupling of the return electrode to the patient. They are intended to reduce electrical resistance of the skin and, by virtue of their own electrical conductivity, to improve electrical contact by filling in any air gaps between the return electrode surface and the patient.

SUMMARY OF THE INVENTION

A principal object of the present invention is to provide a body electrode which is simple and inexpensive to make, which ensures a uniformly good electrical contact area with the body, and which can be sufficiently tightly secured to the body to prevent electrode movement caused by the strain applied by a return cable at its connection to the electrode.

A further object of the invention is to provide a body electrode which is elastic in character and which can be stretched when applying it to the body so that the electrically conductive portion (e.g. a flexible metallic sheet) of the electrode is forced into close and uniformly good electrical contact with the body.

To achieve the foregoing and other unstated but obvious objects, the present invention provides an electrode for use with electro-medical equipment and adapted for attachment to a person's body, said electrode comprising: a stretchable, elastic cover sheet member having an inner surface for facing toward the body and an outer surface for facing away therefrom; a flexible, electrically conductive sheet member positioned with one surface thereof in juxtaposition to the inner surface of the cover sheet member, a first portion of the conductive sheet member being fixedly secured to the cover sheet member, a second portion of the conductive sheet member remaining unsecured to said cover sheet member; terminal means connected in electrically conducting relation to said conductive sheet member; and adhesive means disposed in fixed relation to said cover sheet member for removably attaching the electrode to the body, said adhesive means being positioned at two spaced-apart points spanning the unsecured portion of said conductive sheet member. Preferably, one of the spaced-apart points is in the vicinity of the secured first portion of said conductive sheet member.

According to a preferred embodiment of the invention, the electrode further comprises a stretchable porous inner sheet member adapted to be wetted with an electrically conducting agent and secured to the cover sheet member in the vicinity of the spaced-apart points to thereby sandwich both the fixedly secured portion and the unsecured portion of the conductive sheet member between the inner sheet member and the outer cover sheet member. When such an inner sheet member is provided, it may be expedient to have the adhesive means directly carried by the inner sheet member.

DESCRIPTION OF THE PREFERRED EMBODIMENT

Figure 1:
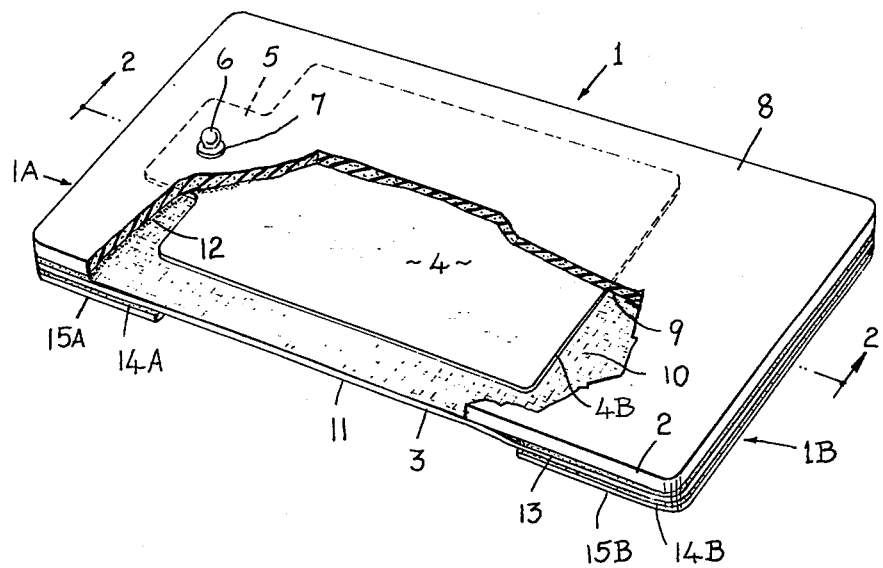
FIG. 1 is a view in perspective showing the outer side of a preferred embodiment of the novel electrode with a portion cut away to reveal the structure thereof.

Referring now to the drawings in detail, wherein like reference characters indicate like parts in the figures, the reference number 1 indicates generally a body electrode constructed in accordance with one preferred embodiment of the invention. The terms "outer" and "inner" as used herein with regard to the constituent elements of the illustrated electrode relate to the position of the elements of their surfaces relative to the person's body or limb against which the electrode 1 is placed, in a direction generally transverse to the body or limb.

In the illustrated embodiment, electrode 1 generally comprises a stretchable, electrically insulating, elastic cover sheet member 2, a stretchable, porous inner sheet member 3, an elongated, flexible, electrically conductive sheet member 4, terminal means 6 adapted for electrical connection to a return cable (not shown), and adhesive means 14A, 14B.

As used herein in relation to cover sheet member 2, the term "elastic" describes its significant tendency to return to its original size, shape or position after being stretched. It has been found that two suitable materials for use in fabricating cover sheet member 2 are rubber and closed-cell foam plastic, which are both capable of being stretched and sufficiently elastic for operation of the electrode as hereinafter described.

Inner sheet member 3, in addition to being stretchable, is preferable porous and therefore capable of being wetted by an electrically conducting agent such as a conventional conducting gel. Suitable materials for inner cover member 3 are porous paper, crepe polyester cloth, and open-cell foam plastic.

Conductive sheet member 4 may be fabricated from a metallic sheet material such as copper or aluminum, which are both highly conductive and sufficiently flexible to conform to the gently convex contours of a limb or other portion of a person's body. Conductive sheet member 4 may also comprise a fabric having epitropic fibres incorporated therein. (Epitropic fibres are capable of conducting electricity due to the fact that fine particles of carbon are embedded in the surface of the fibres).

Figure 2:
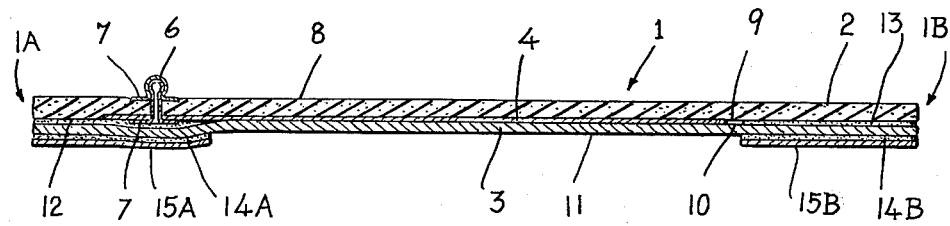
FIG. 2 is an enlarged view in section taken along the line 2—2 of FIG. 1.

As better illustrated in FIG. 2, conductive sheet member 4 is interposed between the cover sheet member 2 and inner sheet member 3, which are all generally rectangular in shape. Conducting element 4 is smaller in size than both the outer member 2 and the inner member 3 (which are generally the same size). Preferably, conductive member 4 is positioned with its perimetric edge in inwardly spaced relation to the perimetric edge of cover sheet member 2 and of inner sheet member 3.

As illustrated, the terminal means, in the form of a conventional male snap fastener 6 having crimped edges 7, is connected in electrically conducting relation to conductive sheet member 4 and fixedly secures the cover sheet member 2 to end portion 5 of conducting sheet member 4 in the vicinity of electrode end 1A.

The cover sheet member 2 has an outer surface 8 and an inner surface 9. Snap fasteners 6 projects through the cover sheet member 2 and provides a connection for secure attachment to an electrical return cable.

The inner sheet member 3 has an inner surface 11 which contacts the person's body and an outer surface 10 which is secured at two spaced-apart joints (generally at electrode ends 1A and 1B) to inner surface 9 of cover member 2 by conventional means, preferably by adhesive coatings designated by the numerals 12 and 13. In the preferred embodiment the adhesive coating 12 also serves to fix the end portion 5 of the conductive member 4 to the outer surface 10 of the inner cover member.

From the foregoing description it will be apparent that conductive member 4 is fixedly secured to both said cover sheet member 2 and said inner sheet member 3 near one end of the body electrode 1, which end is generally designated by the numeral 1A. The opposite end of the body electrode 1 is generally designated by the numeral 1B. The edge 4B of conductive member 4 positioned near the end 1B of the electrode 1 as well as the major portion of the length of conductive member 4 (excepting only end portion 5) remain unsecured to both the inner surface 9 of the cover sheet member 2 and the outer surface 10 of the inner sheet member 3.

Each end of the inner sheet member 3 is provided with adhesive means preferably in the form of pressure sensitive adhesive coatings designated by the numerals 14A and 14B which are positioned at two spaced-apart points in the vicinity of electrode ends 1A, 1B on the inner surface 11 of the inner cover member 3. As will be seen, the two spaced-apart points span the unsecured portion of conductive member 4 (between secured end portion 5 and edge 4B), since this unsecured portion is disposed generally between adhesive coatings 14A and 14B. Conventional "peel off" type covers 15A, 15B are provided to cover the adhesive coatings 14A and 14B while the electrode is in storage.

The use and operation of the invention will now be described with reference to the foregoing detailed description. A conventional conductive gel is first spread over inner surface 11 of the inner sheet member 3 on the area between adhesive coatings 14A and 14B. The conventional "peel off" covers 15A, 15B are then removed from coatings 14A and 14B.

The end 1A of the electrode is then attached to the body by means of the adhesive coating 14A. The opposite end 1B of the electrode 1 is then forcibly gripped by the person applying electrode 1 and the electrode 1 (by reason of the stretchability of cover sheet member 2 and inner sheet member 3) is then stretched over the patient's body (similar to the method of applying a bandaid to a body). The end 1B of electrode 1 is then secured to the body by means of the adhesive coating 14B.

Elastic cover sheet member 2 has thus been stretched over flexible conductive sheet member 4. By reason of the elasticity of the former and the flexibility of the latter, cover sheet member 2 forces the unsecured portion of conductive sheet member 4 to flex into close conformity with the adjacent contours of the body. The unsecured portion of the conductive sheet member 4 is thus forced (over its entire area) against inner sheet member 3 to achieve close and uniformly good electrical contact with the body.

As will be appreciated, the tensioned state of cover sheet member 2 tends to promote a firmer grip upon the body by adhesive coatings 14A, 14B because of the tension force directly between them. As a result, the electrode shows excellent resistance to stresses applied at snap fastener 6 by an electrical return cable connected thereto.

It is to be understood that the particular embodiment of the invention described above and shown in the drawings is merely illustrative and not restrictive on the broad invention. It will be understood by those skilled in the art that various changes in design, structure and arrangement can be made without departing from the spirit of the broader aspects of the invention as defined in the appended claims.

For example, where conductive sheet member 4 is formed of a porous fabric comprising epitropic fibres, the inner sheet member 3 may readily be dispensed with. In accordance with such an embodiment, adhesive coatings 14A, 14B may conveniently be carried by cover sheet member 2 in the vicinity of electrode ends 1A and 1B.

By way of yet another example, conductive sheet member 4 may have its middle portion secured to the cover sheet member 2 (as by fastener 6), thereby leaving both end portions of conductive sheet member 4 unsecured and free to flex under forces applied by a stretched cover member 2.

What I therefore claim is:

1. An electrode for use with electromedical equipment and adapted for attachment to a person's body, said electrode comprising:
   a manually elastically, stretchable, electrically insulating cover sheet member having an inner surface for facing toward the body and an outer surface for facing away therefrom;
   b. an electrically conductive sheet member positioned with one surface thereof in juxta-position to the inner surface of the cover sheet member, a first minor area portion of the conductive sheet member adjacent one end thereof being fixedly secured to the cover sheet member, a second major area portion extending to the other end thereof remaining unsecured to said cover sheet member and thereby adapted to permit relative free movement between the cover sheet member and the electrically conductive sheet member, the electrically conductive sheet member being positioned within ther perimetric edge of the cover sheet member;
   c. terminal means connected in electrically conducting relation to said conductive sheet member;
   d. adhesive means disposed in fixed relation to said cover sheet member for removably attaching the electrode to the body, said adhesive means including first and second separate and distinct adhesive sections, said first section being positioned adjacent one end of the unsecured portion of the conductive sheet member, and the second section being positioned adjacent the opposite end of the unsecured portion of the conductive sheet member and in the vicinity of the secured portion of said conductive sheet member, between whereby said elastically stretchable cover sheet member can be stretched between isolated locations of adhesive attachment of the electrodes to the body and exert refractive force therebetween 2. An electrode as set forth in claim 1, said electrically conductive sheet member comprising epitropic fibres.

3. An electrode as set forth in claim 1, said electrically conductive sheet member being formed from a textile fabric having epitropic fibres incorporated therein.

4. An electrode as set forth in claim 1 and further comprising:
   a stretchable porous inner sheet member adapted to be wetted with an electrically conducting agent and secured to said cover sheet member in the vicinity of said first and second adhesive sections to thereby sandwich both the fixedly secured protion and the unsecured portion of said conductive sheet member between the inner sheet member and said cover sheet member.

5. An electrode as set forth in claim 4 wherein said adhesive means is carried by said stretchable porous inner sheet member.

6. An electrode as set forth in claim 4 wherein said electrically conductive sheet member is formed of metallic sheet material.

7. An electrode as set forth in claim 4 wherein said electrically conductive sheet member comprises epitropic fibres.

8. An electrode for use with electromedical equipment and adapted for attachment to a person's body, said electrode comprising:
   a. a manually elastically stretchable, electrically insulating cover sheet member having an inner surface for facing toward the body and an outer surface for facing away therefrom;
   b. a stretchable porous inner sheet member having an inner surface for facing toward the body and an outer surface for facing away therefrom, said porous inner sheet member being adapted to be wetted with an electrically conducting agent and secured at two spaced apart points on the outer surface thereof to the inner surface of the cover sheet member, said inner sheet member being substantially the same size as said cover sheet member;
   c. an elongated electrically conductive sheet member positioned between, and having one end portion thereof fixedly secured to, said cover sheet member and the inner sheet member, the remaining portion of the conductive sheet member constituting the major portion of the surface area thereof remaining unsecured to both said cover sheet member and said inner sheet member and thereby adapted to permit relative free movement between the elastic cover sheet member and the electrically conductive sheet member over said major area portion; said conductive sheet member being smaller than both the cover sheet member and said inner sheet member and being positioned with its perimetric edge in inwardly spaced relation to the perimetric edges of the cover sheet member and of the inner sheet member;
   d. terminal means connected in an electrically conducting relation to said conductive sheet member and extending through the cover member to project outwardly thereof; and
   e. adhesive means carried by said inner sheet member for removably attaching the electrode to the body, said adhesive means being positioned on the inner surface of the inner sheet member and having first and second separate and distinct adhesive sections, said first section being positioned adjacent one end of the unsecured portion of the conductive sheet member, and the second section being positioned adjacent the opposite end of the unsecured portion of the conductive sheet member and in the vicinity of the secured portion of said conductive sheet member, whereby said elastically stretchable cover sheet member can be stretched between isolated locations of adhesive attachment of the electrode to the body and exert retractive force therebetween.

9. An electrode as set forth in claim 8, said conductive sheet member being formed of metallic sheet material and said terminal means comprising the male portion of a snap fastener.

10. An electrode as set forth in claim 8, said terminal means being disposed in the vicinity of, and outwardly from the second section at which said adhesive means is positioned.

* * * * *